United States Patent [19]
Bokros

[11] Patent Number: 4,863,458
[45] Date of Patent: Sep. 5, 1989

[54] HEART VALVE PROSTHESIS HAVING CONFIGURED LEAFLETS AND MOUNTING EARS

[75] Inventor: Jack C. Bokros, Austin, Tex.

[73] Assignee: Carbomedics Inc., Austin, Tex.

[21] Appl. No.: 284,254

[22] Filed: Dec. 14, 1988

[51] Int. Cl.$^4$ .............................................. A61F 2/24
[52] U.S. Cl. ................................... 623/2; 137/512.1; 137/527
[58] Field of Search ................. 623/2; 137/512.1, 527, 137/827.8

[56] References Cited

U.S. PATENT DOCUMENTS

| | | | |
|---|---|---|---|
| 4,159,543 | 7/1979 | Carpentier | 623/2 |
| 4,308,624 | 1/1982 | Klawitter | 623/2 |
| 4,357,715 | 11/1982 | Klawitter | 623/2 |
| 4,443,894 | 4/1984 | Klawitter | 623/2 |
| 4,451,937 | 6/1984 | Klawitter | 623/2 |
| 4,689,046 | 8/1987 | Bokros | 623/2 |

FOREIGN PATENT DOCUMENTS 0211576  2/1987  European Pat. Off. ................ 623/2

*Primary Examiner*—Ronald L. Frinks
*Attorney, Agent, or Firm*—Russell J. Egan; John R. Merkling

[57] ABSTRACT

A heart valve prosthesis having an annular valve body, a pair of leaflet occluders mounted therein for pivoting and translational movement between closed and open positions. Leaflet occluders have mating diametrical edges and arcuate edges which engage the valve body when the leaflets are closed. Generally frustoconical mounting ears extend outwardly from the leaflet edge, adjacent the diametrical edge thereof. The ears are received in recesses formed in the annular body. The recesses have an upper section extending in the direction of blood flow and a downstream section inclined thereto in a direction extending outwardly. The leaflets each have a flat upstream surface and a generally cylindrical downstream surface.

7 Claims, 2 Drawing Sheets

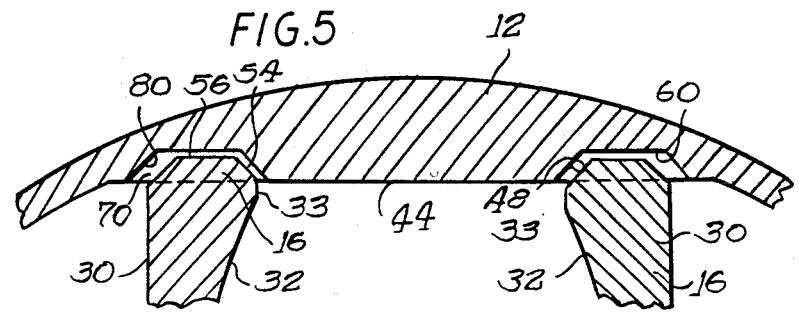
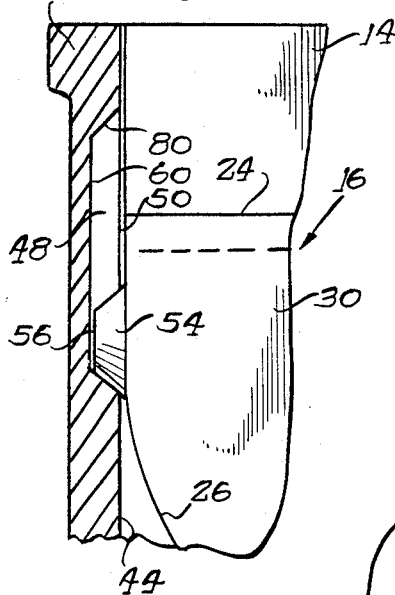
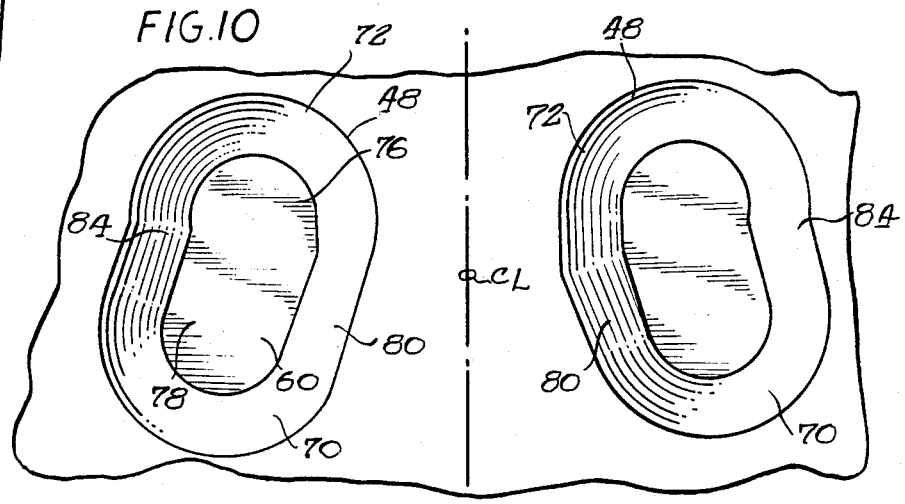
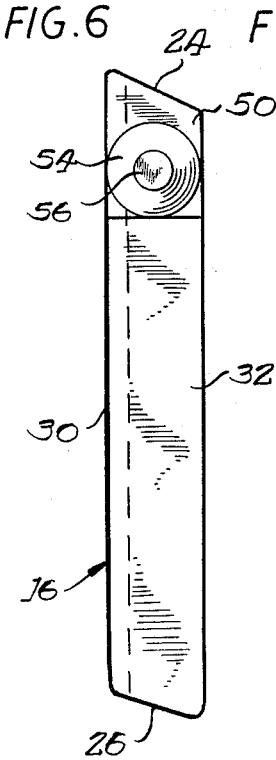
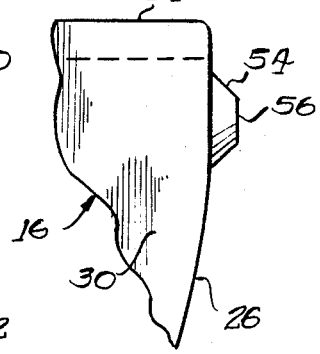
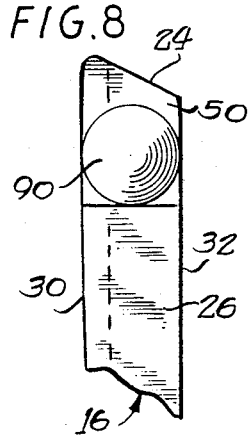
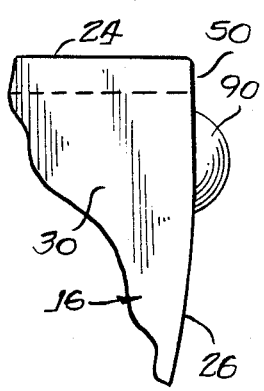
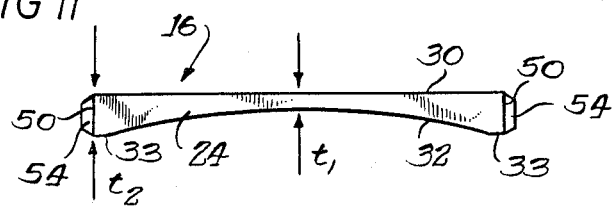

HEART VALVE PROSTHESIS HAVING CONFIGURED LEAFLETS AND MOUNTING EARS

BACKGROUND OF THE INVENTION

1. Field of the Invention

The present invention pertains to heart valve prostheses and in particular, to bileaflet heart valve prostheses using pivotable valve members.

2. Description of Related Art

Various types of heart valve prostheses have been developed which operate hemodynamically, that is, by the pumping action of the heart. Although, upon cursory observation, such heart valve prostheses appear to be relatively simple mechanisms functioning merely as check valves, considerable effort has been expended in their design and improvement, due principally to their life support function.

Heart valve prostheses are movable between an open position to allow blood flow in a downstream direction and a closed position to minimize regurgitation of blood in an upstream direction. Because hemodynamic energy alone is relied upon for proper operation of the heart valve between opened and closed positions, it is generally desirable to reduce friction losses in the heart valve which would needlessly burden the cardiac system. The interfitting occluders and heart valve body, which is typically annular in configuration, are usually designed with a certain amount of "play". A relatively loose fitting engagement between the occluders and the valve body reduces friction losses and is one technique employed to eliminate the possibility of binding of the occluders.

Considerable attention has been paid to bileaflet heart valves of the type having a pair of opposed leaflets which are generally semicircular in shape and which have abutting diametrical edges that are joined together during valve closing. A number of different arrangements have been proposed for pivotally mounting leaflets within an annular valve body and, despite efforts which have been devoted to the operational reliability and low friction operation of these devices, further improvements can be made. For example, U.S. Pat. No. 4,443,894 provides leaflet occluders having generally opposed upstream and downstream generally flat surfaces and which are generally wedge-shaped in cross-sectional profile. The leaflets are pivotally mounted within valve body depressions by hemispherical projections or mounting ears. Outwardly extending from the leaflets, adjacent the diametrical edge thereof. The depressions in the valve body are shaped with a generally spherical contour for cooperation with the spherical projections. Over the countless number of operations of a heart valve, the projections and depressions are subjected to wear. For the reasons set forth in U.S. Pat. No. 4,689,046, spherical projections and depressions are susceptible to significant amounts of "play" in directions lying in the plane of the leaflet and extending generally perpendicular to the diametrical edge thereof. It has been observed that relatively small amounts of wear adjacent the tip of the spherical projection or the corresponding center portion of the recess results in a significant amount of lateral play, even for relatively minute amounts of increased "end play" that is, in directions generally parallel to the diametrical leaflet edge and extending along the hinge points of a leaflet. As a result of this lateral play, the motion and the sequence, especially the synchronous cooperation of the leaflets becomes less well defined. As a result, performance of the leaflet may become erratic, as is evidenced, for example, by an asynchronous closure of the valve. While in general, prior art heart valves have proven to be very reliable, and have in general been shown to have a projected life expectancy exceeding that of the patient, it is desirable to achieve increased margins of safety by providing a prosthesis which substantially exceeds reliability and performance requirements.

SUMMARY OF THE INVENTION

It is an object of the present invention to provide an improved heart valve having a novel construction which can be made from pyrocarbon or other suitable materials.

Another object of the present invention is to provide a heart valve including a pair of leaflets which have projections for mounting to an annular valve body and which cooperate with the valve body to reduce the amount of play, particularly lateral play as defined above, despite wear on the rotating mounting components.

These and other objects will become apparent from studying the appended description and drawings which relate to a heart valve prosthesis for allowing blood flow therethrough in a downstream direction, said valve prosthesis comprising:

a generally annular valve body having an interior surface defining a central passageway through which blood flows;

a pair of leaflet occluders proportioned to be pivotally received within said valve body and to move between an open position and a closed position wherein they block the reverse flow of blood in an upstream direction, said leaflet occluders each having a generally flat upstream surface, a diametrical edge for mating with the other occluder and an arcuate edge, having outwardly protruding generally conical ears generally adjacent the diametrical edge for pivotal mounting to said valve body; and said valve body defining for each leaflet occluder, a pair of generally V-shaped ear-receiving recesses for pivotally mounting the ears of said leaflet, with each V-shaped recess for mounting an ear of one occluder including an upstream section with an upper end and a downstream section with a lower end, the downstream section being angularly offset with respect to said upstream section in a direction away from a centerline plane of the valve body, said upstream and said downstream sections being tapered in the direction of their depth to provide a complementary fit with a conical ear received therein and said upstream and said downstream sections being configured to provide both pivoting and translation movement of an ear received therein as the ear is moved during opening and closing of said valve.

BRIEF DESCRIPTION OF THE DRAWINGS

Referring now to the drawings, wherein like elements are referenced alike,

FIG. 4 is a fragmentary view taken partly in cross-section along the line 4—4 of FIG. 2;

FIG. 5 is a fragmentary cross-sectional view taken along the line 5—5 of FIG. 2;

FIG. 6 is a side elevational view of a leaflet of the preceding Figures;

FIG. 7 is a fragmentary plan view of one corner of the leaflet of FIG. 6 showing the mounting ear thereof;

FIGS. 8 and 9 are fragmentary side elevational and plan views of a leaflet similar to that of the preceding Figures but having part spherical mounting ear;

FIG. 10 is a fragmentary elevational view taken from the inside of the valve body; and FIG. 11 is an end elevational view of the leaflet of the preceding Figures.

DETAILED DESCRIPTION OF THE PREFERRED EMBODIMENT

Figure 1:
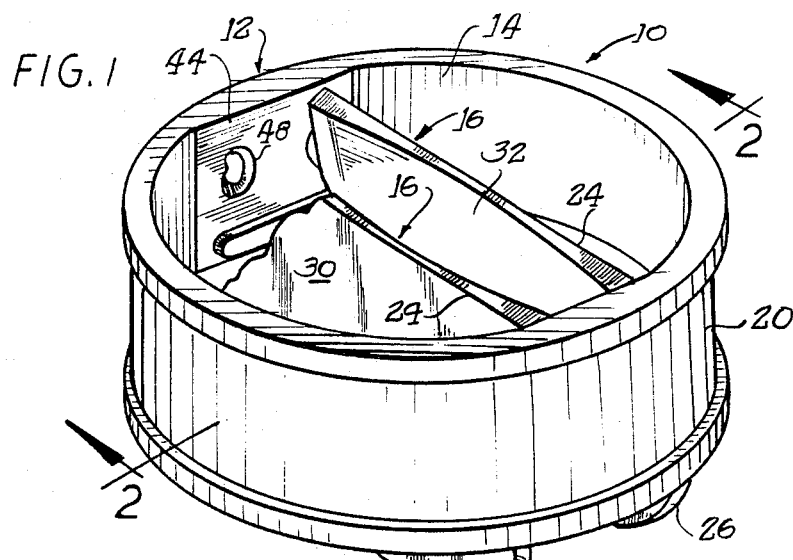
FIG. 1 is a perspective view of a heart valve prosthesis illustrating certain aspects of the present invention.

Referring now to the drawings, a heart valve prosthesis is generally indicated at 10. The prosthesis 10 includes a generally annular valve body 12, having an inner cylindrical surface 14. Disposed within the valve body are a pair of valve occluders or leaflets 16. The leaflets 16, as will be seen, are mounted for both pivoting and translational movement between opened and closed positions. The outside surface of valve body 12 includes an annular recess or depression 20 for accommodating a suturing ring (not shown) of a conventional type for suturing the heart valve 10 to the heart tissue. As will be seen, the hinge mechanism supporting the leaflet 16 is protected by the valve body against contact with heart tissue or any unraveled sutures which might be present in the immediate area.

The leaflets 16 have an outer edge which extends between upstream and downstream surfaces. The outer edge includes an inner diametrical edge portion 24 which is opposed by an arcuate, and more particularly a semicircular edge portion 26. According to one aspect of the present invention, the upstream major surfaces 30 of leaflets 16 are generally flat and semicircular in shape. The opposed downstream surface 32 is generally concave in shape, and is preferably part cylindrical in configuration, with the axis of the cylinder lying below the leaflet in a mid plane of the leaflet which extends normal to both the leaflet upper surface and the leaflet diametrical edge portion 24. The leaflets 16 are preferably symmetrical about the mid plane thereof. The concave downstream surface 32 is shown in the perspective view of FIG. 1, and is best seen in FIG. 11, which also shows the leaflet symmetry.

As mentioned above, the valve body 12 has a generally annular configuration with an inner cylindrical surface 14. The cylindrical surface 14 extends throughout most of the valve body interior, except for raised flat surfaces 44 which are generally parallel to one another, extending across chords of the inner cylindrical surfaces 14, and having a valve body mid plane extending along the diametrical plane of body 12 at which edge portions 24 are mated upon valve closing. As will be seen, the heart valve prosthesis of the preferred embodiment is symmetrical about the valve body mid plane, with the recesses and leaflets being mirror images of one another. Recesses 48 are formed in flat surfaces 44 to provide a hinge mounting for the leaflets 16. Two recesses are required for the mounting of each leaflet, and are located adjacent the diametrical edge of that leaflet.

Referring briefly to FIG. 4, the arcuate edge portion 26 of a leaflet is blended into a relatively flat, lateral edge portion 50 adjacent the diametrical edge portion 24. The lateral edge portion 50 provides a relatively close fit with respect to the flat surface 44. According to one aspect of the present invention, the relative size of flat surface 44 as compared to the inner cylindrical surface 14, is made as small as possible to minimize impeding blood flow through the heart valve prosthesis and to also minimize turbulence in the flow. Generally frustoconical outward projections or mounting ears 54 extend from the flat edge portions 50 of a leaflet. The ears 54 have a generally disk-like free end surface 56 which faces toward the bottom or innermost end surface 60 of recess 48.

Figure 2:
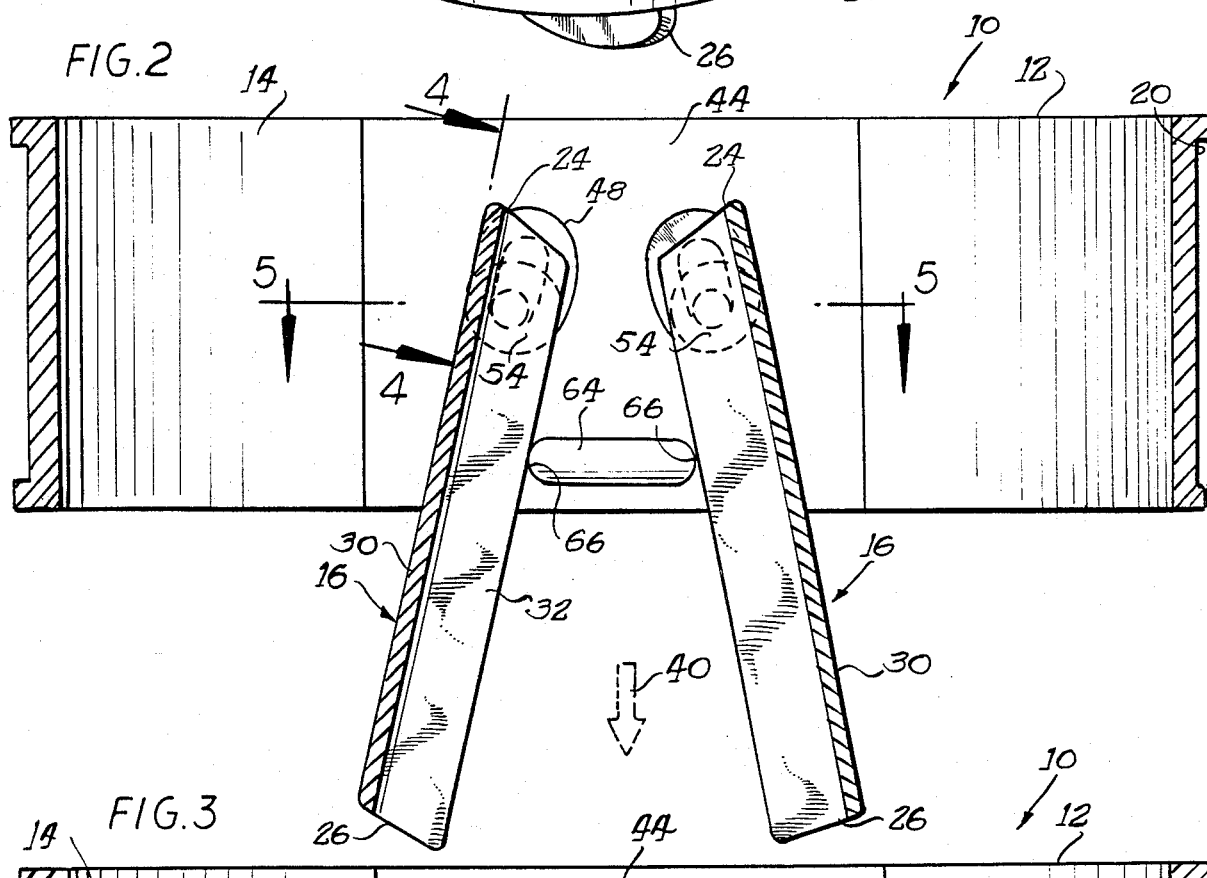
FIG. 2 is a cross-sectional view taken along the line 2—2 of FIG. 1, showing the valve in an open position.

For reasons which will become apparent herein, the upstream and downstream surface configurations of leaflets 16 offer a number of advantages. For example, the relatively flat upstream surface 30 imparts a stiffness to the leaflets, preventing their unintentional disengagement from a pivotal mounting connection with the valve body. Referring to FIG. 2, the prosthesis 10 is shown in a generally open configuration with the axes of the generally cylindrical downstream surfaces extending generally in the direction of blood flow, indicated by arrow 40. The generally concave cylindrical downstream surfaces 32 provide, in addition to a streamlining effect, a leaflet of reduced cross sectional thickness, thereby aiding in eliminating a drag of the blood flow on the leaflet surfaces.

Referring to FIG. 11, leaflet 16 is shown in an end elevational view, facing the diametrical edge 24 of the leaflet. The upper generally flat surface 30 extends between the lateral edges 50 of the leaflet. In the preferred embodiment, the generally part cylindrical downstream surface 32 extends nearly the same distance, that is, immediately adjacent the lateral edges 50 of the leaflet, but preferably is extended by relatively flat portions 33. The flat extensions 33 can be eliminated, if desired. As can be seen in FIG. 11, the leaflet midplane thickness $t_1$, taken along a central plane of the leaflet, is substantially smaller than the thickness $t_2$ taken at the leaflet lateral edge. The generally conical mounting ears 54 have a base as large as or slightly smaller than the thickness $t_2$ at the lateral edge of the leaflet so as to avoid any protrusion beyond the upstream or downstream surfaces 30,32 of the leaflet. The mounting ears 54, as can be seen with additional reference to FIGS. 4, 6 and 7, for example, are located adjacent the diametrical edge 24 and extend outwardly from the lateral edges 50 in generally opposite directions.

The different curvatures of the upper and lower surfaces of the leaflet conveniently provide regions of increased strength immediately adjacent the mounting ears 54 where the concentration of stress is high, while significantly reducing the mass of the leaflet at the central portion thereof. As will be seen, leaflet cross-sectional configurations corresponding generally to the shape illustrated in FIG. 11, provide other advantages which improve valve operation. For example, in addition to the increased stiffness provided by upstream surface 30, the downstream surface 32 of the leaflet guides upstream blood flow in a manner which accelerates the valve closing. These and other advantages will be discussed further herein.

Figure 3:
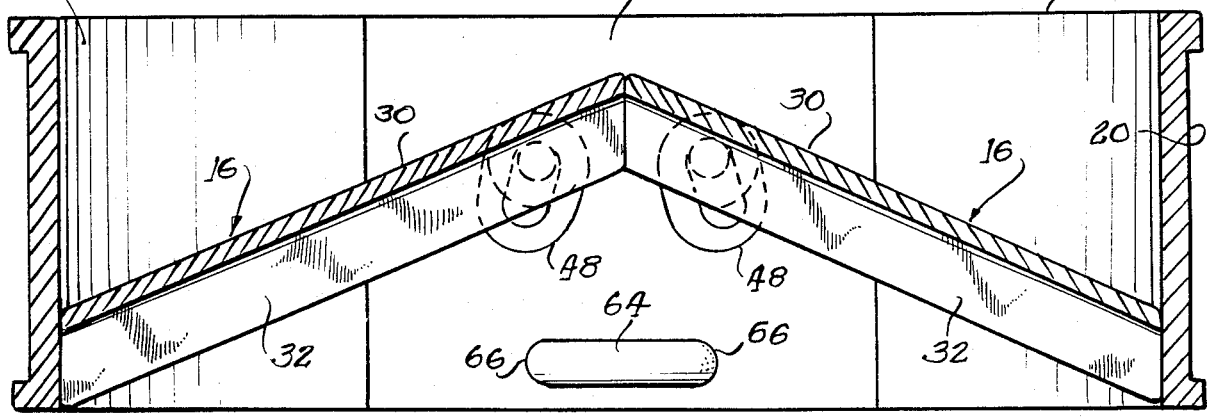
FIG. 3 is a cross-sectional view similar to that of FIG. 2 but showing the valve in closed position.

Referring now to FIGS. 2 and 3, the leaflets 16 are moved between open and closed positions in response to blood flow through valve 10. In the open position of FIG. 2, downstream edges of leaflets 16 contact an abutment member 64 having a pair of opposed rounded end surfaces 66 engageable with the downstream outer edges of the leaflets. As indicated in FIG. 2, the ears 54 are positioned adjacent the lower ends 70 when the leaflets are in a fully open position with their downstream edges contacting the rounded ends 66 of abutment means 64.

As the cardiac cycle continues, the leaflets 16 move to the closed position illustrated in FIG. 3. In the closed position, the ears 54 are positioned adjacent the upper ends 72 of recesses 48. Referring to FIG. 10, the centerline plane CL of the heart valve divides or separates the recesses associated with two different leaflets. Thus, the two recesses illustrated in FIG. 10 each support an edge of a leaflet. As can be seen most clearly in FIG. 10, the recesses 48 may have a dogleg or generally V-shaped configuration with an upper section 76 extending generally parallel to the centerline plane CL and a lower section 78 inclined away from the centerline plane. The recesses 48 include a bevelled perimetrical side wall 80 which, as can be best seen in FIG. 5, is bevelled in the direction of its depth to have a configuration corresponding to the conical configuration of ears 54. As can be seen in FIG. 5, the recess 48 has an opening of lateral width greater than the size of the conical ears 54 so as to allow ear to travel back and forth, toward and away from centerline plane CL during leaflet opening and closing. The increased width of the recess provides a clearance which eliminates binding of the ears in their extreme positions (which are illustrated in FIGS. 2 and 3).

In operation, the leaflet mounting ears 54 undergo both a pivoting and a translation displacement as the leaflets are moved between their closed and open positions. Referring initially to FIG. 2, with the leaflets in the fully open position, leaflet ears 54 rest against the lower ends 70 of recess 48. As shown in FIG. 4, the conical outer surface of the leaflet mounting ear rests against the lower end 70 of side wall 80. As back force is exerted on the downstream surface 32 of the leaflets, the leaflets are pivoted such that their lower free ends 26 are swung in outward directions corresponding to a pivoting of ears 54 within the recesses.

Due to the elongated path of travel of the ear as defined by the cooperation between the upper and lower recess segments 76, 78 the leaflets are free to undergo a translational movement toward the upper ends 72 of the recesses. During this displacement toward a closed position, the ears wipe across portions of the outer recess segments 84, which segments are remote from the centerline plane CL. This action provides a cleaning of the recess. In addition, due to the bevelled side walls 80 of the recesses, a flow of blood flushes the recesses during valve operation. The concave downstream surfaces of the leaflets enhance the capture of blood flow under the leaflet and discourage bypass of the back flow around the lower ends of the leaflets, as is more likely to occur with leaflets having generally flat downstream surfaces. Due to the increased capture of blood flow, the force applied to the leaflet downstream surfaces is increased and the leaflets are closed more quickly, thus decreasing the amount of regurgitation in each cardiac cycle.

As can be seen from FIG. 10, the configuration of the constraining recesses 48, causes the leaflet translational movement during closing to occur in an upward and inward direction. Toward the end of the leaflet travel, the leaflets travel in an upstream direction, opposite that of arrow 40 (see FIG. 2). As seen in FIG. 2, the bottom edges of the leaflets are bevelled and, in the final portion of their upstream travel, seat against the lower portion of the valve body inside surface 14. The leaflets assume a fully closed position with the diametrical edge portions 24 thereof engaging each other. It is not necessary that the ears 54 engage the uppermost portion of recess side wall 80 and accordingly, unnecessary wear can be avoided. However, it is generally preferred that the ears 54 be positioned immediately adjacent the uppermost portion of recess side wall 80.

During opening, downstream directed blood flow applies force against the upstream surfaces 30 of the leaflets. Due to the positioning of their pivot mounting, leaflets 16 are subjected to a relatively large torque, as a result of forces applied across the upstream surfaces of the leaflets. This results in a relatively rapid initial opening of the leaflets which easily overcomes any resistance thereto. The opening force also breaks the seal between the diametrical edge portions 24 of the leaflets, and between their lower bevelled edges 26 and the inside valve surface 14.

Due to the afore-described configuration of the recesses 48, the leaflets initially undergo a downstream translational and pivoting displacement. The downstream translation continues for a brief portion of time until the ears 54 enter the lower section 78 of the recesses. The leaflet ears may be slightly shifted, with their displacement being directed downwardly and outwardly. During this time, the leaflet ears also continue to undergo pivoting movement with the leaflets swinging toward each other. Downward displacement continues until the ears engage the lower end of recess side wall 80, as illustrated in FIGS. 2 and 4. Inward swinging of the leaflets continues until their downstream edges contact the rounded ends 66 of abutment means 64. During opening, the concave configuration of downstream leaflet surfaces 32 provides increased clearance for blood flow in a downstream direction, as compared to relatively flat leaflets of comparable thickness adjacent their diametrical or mating ends.

As mentioned, the leaflets 16 preferably each have a relatively flat upstream surface 30. This enhances the stiffness of the leaflet to withstand bending deflections which could "cup" the leaflet, effectively shortening the distance between its opposed ears 54 and thus increasing the possibility that the ears might become disengaged from the recesses 48. Such cupping, if allowed to occur, would likely be in a direction tending to exaggerate the concavity of the downstream surface. The increased stiffness provided by the relatively flat upstream surface effectively precludes such bending and any attendant dislodgment of the leaflet from the valve body.

As will now be seen, the preferred configuration of leaflets 16 provide several advantages in a leaflet design of relatively minimal mass. First, the concave downstream surface configuration of the leaflets captures blood flow and increases force applied to the leaflets accelerating their closing and thereby lessening regurgitation through the valve. The relatively flat upstream surface of the leaflets increases their stiffness, and greatly improves resistance to bending thus ensuring the captivity of the leaflet mounting ears within the recesses of the valve body. This is an important advantage particularly for relatively thin leaflets which can be constructed from material sufficiently flexible to permit their snap-in installation. This of course cooperates with the capture of upstream blood flow effectively allowing the leaflets to close promptly.

Referring to FIGS. 6 and 7, leaflet 16 is shown with generally conical ears 54, as described above. The conical configuration of the ears is preferred because that shape results in less play over the entire life of the valve prosthesis, particularly as the valve suffers a certain amount of inevitable wear. Even should noticeable wear occur at the end faces 56 of the conical ears, a much smaller increase in lateral play of the leaflet (in directions generally normal to the flat upstream surface) is experienced, compared to leaflet ears of other configurations, such as the popular spherical configuration illustrated in FIGS. 8 and 9.

Referring now to FIGS. 8 and 9, a leaflet 16 illustrated therein is identical to the leaflet 16 described above in the foregoing Figures, except that the conical ears 54 are replaced with generally hemispherical ears 90. As was explained in U.S. Pat. No. 4,689,046, herein incorporated by reference, small amounts of wear in the outer surface of the hemispherical ears, such as the ears 90 of FIGS. 8 and 9 results in a more substantial lateral play of the leaflets than is experienced in the preferred truncated conical ears. Additional advantages are realized when conical ears are employed over spherical ears in that, when nested in a similarly contoured recess, the conical ears establish a line contact with the bevelled side walls of the recess, whereas the spherical ears of FIGS. 8 and 9, if worn unevenly, tend to establish one or more point contacts with their cooperating, similarly configured recesses.

The mating leaflet ears and cooperating recesses of the preferred embodiment are expected to exhibit a very uniform level of wear over the expected life of a patient fitted with the heart valve 10. This is due in part to the lateral clearance as illustrated in FIG. 5 and the elongated, bevelled path of the recesses as illustrated in FIG. 10 which allow the leaflet mounting ears 54 to "float" free of significant frictional contact with the recess sidewalls as the leaflet is moved between open and closed positions. However, even though the leaflet operates with a relatively low friction, the movement of the leaflets is well controlled throughout the life of valve 10 because of the cooperating conical ears and complementary-shaped recesses in which the ears ride.

As can be seen, a heart valve prosthesis according to principles of the present invention offers a number of significant improvements and advantages. For example, the configuration of the leaflet cross section provides a leaflet of reduced, minimal mass whose upper surface increases stiffness and prevents disengagement of the leaflet mounting with the valve body. The downstream surface configuration reduces leaflet mass and improves the capture of blood flow with an attendant application of force to the downstream surface of the leaflet thereby accelerating valve closing and lessening regurgitation. Further, the leaflet cross-sectional configuration conveniently provides lateral edges of localized increased mass immediately adjacent the leaflet mounting ears where stress on the leaflet is high.

The preferred leaflet configuration, where leaflet thickness is increased at the lateral edges, also provides a mounting surface for the mounting ears of increased size, thus ensuring that the mounting ears do not protrude beyond the upstream and downstream major leaflet surfaces. This latter feature is particularly important for the preferred frustoconical mounting configuration which has an enlarged base portion at its point of joinder with the leaflet edge. The frustoconical mounting ears reduce lateral play of the leaflet despite inevitable wear experienced throughout the patient's life. Reduced wear, especially compared to that of spherical mounting ears, maintains control over leaflet movement and prevents erratic leaflet operation such as asynchronous closing.

Recesses formed in the annular valve body may have a dog leg or V-shape with mating recesses which are bevelled to have a shape complementing that of the conical leaflet ears. The recesses are enlarged with respect to the mounting ears to provide smooth, low friction operation of the leaflet during opening and closing with a considerable portion of the leaflet travel comprising a translational "floating" which is substantially free of frictional engagement with the recess mating edges.

A description of the present forms of the invention having been described by way of example, it is anticipated that variations of the described forms of the apparatus may be made without departing from the invention and the scope of the appended claims.

What is claimed is:

1. A heart valve prosthesis for allowing blood flow therethrough in a downstream direction, said heart valve prosthesis comprising:
   a generally annular valve body having an interior surface defining a central passageway through which blood flows;
   a pair of leaflet occluders proportioned to be pivotally received within said valve body and to move between an open position permitting blood flow in a downstream direction and a closed position blocking the reverse flow of blood in an upstream direction, said leaflet occluders each having a generally flat upstream surface, an opposed generally concave downstream surface, a diametrical edge between the upstream and downstream surfaces for mating with the other occluder and an arcuate edge also between the upstream and downstream surfaces and having outwardly protruding generally conical mounting ears adjacent the diametrical edge for pivotal mounting to said valve body; and
   said valve body defining for each leaflet occluder, a pair of generally V-shaped ear-receiving recesses for pivotally mounting the ears of said leaflet, with each V-shaped recess including an upstream section with an upper end and a downstream section with a lower end, said upstream and said downstream sections being tapered in the direction of their depth to provide a complementary fit with a conical ear received therein and said upstream and said downstream sections configured to provide both pivoting and translation movement of an ear received therein as the ear is moved during opening and closing of said valve.

2. The heart valve prosthesis of claim 1 wherein said arcuate edge is generally semicircular.

3. The heart valve prosthesis of claim 1 wherein said concave downstream surface has a generally partially cylindrical configuration.

4. The heart valve prosthesis of claim 1 further comprising abutment means on said valve body beneath a pair of recesses, each associated with a respective occluder.

5. The heart valve prosthesis of claim 1 wherein said downstream section is angularly offset with respect to said upstream section.

6. A heart valve prosthesis comprising:
- a generally annular valve body having an interior surface defining a central passageway through which blood flows;
- a pair of leaflet occluders proportioned to be pivotally received within said valve body and to move between an open position permitting blood flow in a downstream direction and a closed position blocking the reverse flow of blood in an upstream direction, said leaflet occluders each having a body portion with a generally flat upstream surface, an opposed generally concave downstream surface, and an outer perimetrical edge between the upstream and downstream surfaces, said perimetrical edge including a diametrical edge portion for mating with the other occluder upon valve closing, an arcuate edge opposite the diametrical edge for engagement with the valve body during valve closing, and relatively flat lateral edge portions between the arcuate and diametrical edge portions;
- generally frustoconical mounting ears generally adjacent the diametrical edge portion, and extending from respective lateral edge portions in opposing directions;
- said occluders having a thickness between the upstream and downstream surfaces thereof, said thickness being a minimum in a midplane normal to the upstream surface and to the diametrical edge, and the occluder having a significantly increased thickness at the lateral edge portions where the mounting ears are joined to the leaflet body; and
- said valve body defining for each leaflet occluder, a pair of generally V-shaped ear-receiving recesses including an upstream section with an upper end and a downstream section with a lower end, said upstream and said downstream sections being tapered in the direction of their depth to form bevelled ear-engaging sidewalls having a complementary fit with a conical ear received therein and said upstream and said downstream sections configured to provide both pivoting and translation movement of an ear received therein during opening and closing of said valve.

7. The heart valve prosthesis according to claim 6 wherein said downstream section is angularly offset with respect to said upstream section.

* * * * *